(12) United States Patent
Schulz et al.

(10) Patent No.: US 6,852,898 B2
(45) Date of Patent: Feb. 8, 2005

(54) METHOD FOR PRODUCING OLIGOMERS

(75) Inventors: Ralf Schulz, Speyer (DE); Thomas Heidemann, Weinheim (DE); Peter Schwab, Bad Duerkheim (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 64 days.

(21) Appl. No.: 10/221,168

(22) PCT Filed: Mar. 22, 2001

(86) PCT No.: PCT/EP01/03262

§ 371 (c)(1),
(2), (4) Date: Sep. 18, 2002

(87) PCT Pub. No.: WO01/72670

PCT Pub. Date: Oct. 4, 2001

(65) Prior Publication Data

US 2003/0130550 A1 Jul. 10, 2003

(30) Foreign Application Priority Data

Mar. 25, 2000 (DE) ......................... 100 15 002

(51) Int. Cl.$^7$ ............................ C07C 2/06; C07C 2/08; C07C 2/10
(52) U.S. Cl. ........................................ 585/531; 585/530
(58) Field of Search ............................... 585/531, 530

(56) References Cited

FOREIGN PATENT DOCUMENTS

| DE | 19910103 | 3/1999 |
| DE | 199 22 038 | 11/2000 |
| WO | 99 25668 | 5/1999 |

*Primary Examiner*—Thuan D. Dang
(74) *Attorney, Agent, or Firm*—Oblon, Spivak, McClelland, Maier & Neustadt, P.C.

(57) ABSTRACT

In a process for preparing essentially unbranched oligomers of alkenes having from 4 to 6 carbon atoms starting from the alkenes or a hydrocarbon stream comprising such alkenes over a nickel-containing heterogeneous catalyst in an adiabatically operated reactor at from 20 to 300° C. and pressures of from 1 to 100 bar, a first substream of the output from the reactor is worked up to isolate the oligomers and the second substream is recirculated together with fresh alkene or a fresh hydrocarbon stream comprising such alkenes to the reactor.

20 Claims, 1 Drawing Sheet

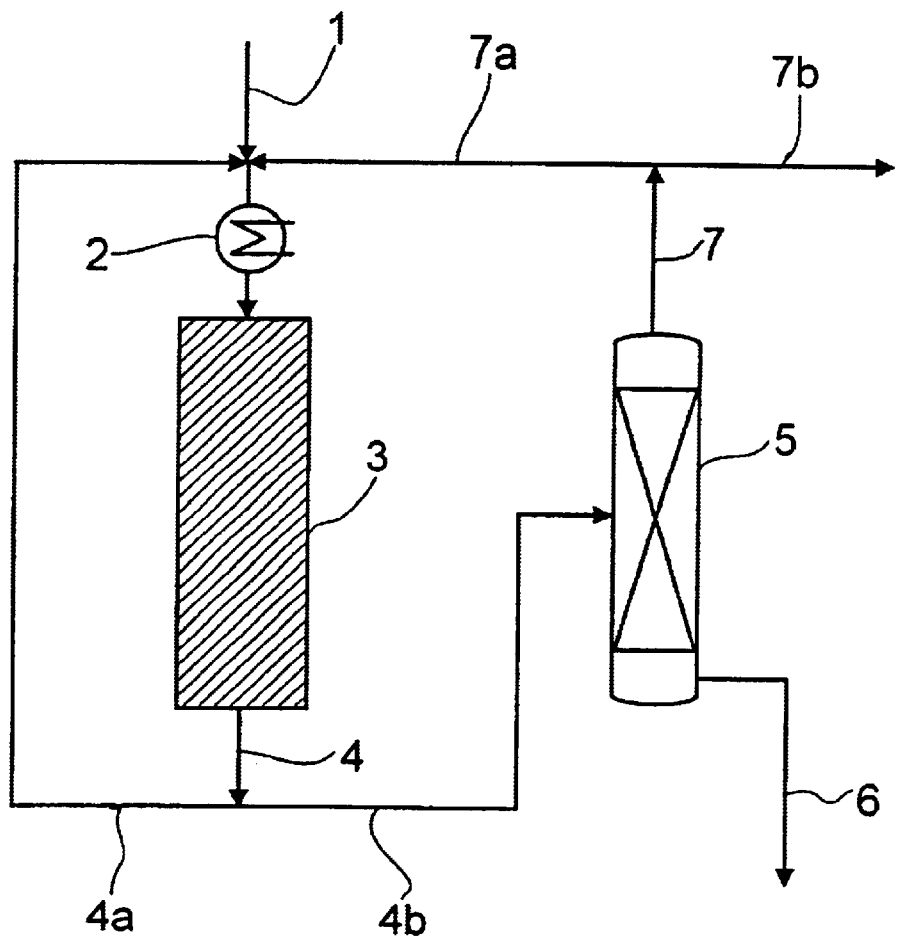

METHOD FOR PRODUCING OLIGOMERS

The present invention relates to a process for preparing essentially unbranched oligomers of alkenes having from 4 to 6 carbon atoms starting from the alkenes or a hydrocarbon stream comprising such alkenes over a nickel-containing heterogeneous catalyst in an adiabatically operated reactor at from 20 to 300° C. and pressures of from 1 to 100 bar.

Alkenes having from 2 to 6 carbon atoms and mixtures thereof, in particular alkenes having 4 carbon atoms, are available in large quantities both from FCC plants and from steam crackers. The respective $C_4$ fraction, i.e. the mixture of butenes and butanes, is, after removal of the isobutene, very well suited to the preparation of oligomers, in particular octenes and dodecenes. Both the octenes and dodecenes can be converted by hydroformylation and subsequent hydrogenation into the corresponding alcohols which can be used, for example, for the preparation of plasticizers.

Here, the degree of branching of the plasticizer alcohol has a decisive effect on the properties of the plasticizer. The degree of branching is described by the ISO index which indicates the mean number of methyl branches in a fraction comprising isomeric compounds having hydrocarbon chains, here specifically of alkenes and of the alcohols derived therefrom. Thus, for example, n-octenes with 0, methylheptenes with 1 and dimethylhexenes with 2 contribute to the ISO index of a fraction. In other words: the lower the ISO index, the more linear the molecules in the respective fraction. In turn, the higher the linearity, i.e. the lower the ISO index, the higher the yields in the hydroformylation and the better the properties of the plasticizer prepared therefrom.

The earlier German patent application having the file number 199 10 103.5 teaches a process for the oligomerization of $C_6$-alkenes by reaction of a $C_6$-alkene-containing reaction mixture over a nickel-containing fixed-bed catalyst, in which process it is important that not more than 30% by weight of the $C_6$-alkenes, based on the reaction mixture, are reacted. Unreacted $C_6$-alkene can be separated from oligomeric products and be returned to the reaction.

Furthermore, WO-A 99/25668 discloses a process for preparing essentially unbranched octenes and dodecenes, in which hydrocarbon streams comprising 1-butene and/or 2-butene and butane are reacted over a heterogeneous nickel-containing catalyst. In this process, the butane and unreacted butene separated from the reaction mixture are recirculated to the oligomerization reaction in such amounts that the maximum oligomer content of the unconverted reaction mixture does not exceed 25% by weight at any place in the reactor.

The oligomerization of low molecular weight alkenes is generally accompanied by noticeable evolution of heat. In a reaction over a heterogeneous catalyst under adiabatic conditions, virtually all the heat of reaction is removed from the reactor by the reaction mixture. This means that the throughput through the reactor and thus also the conversion per unit time essentially have to be adjusted according to the quantity of heat which is to be removed from the reactor. For this reason, a person skilled in the art will feed the alkene stream into the reactor and adjust the other reaction parameters so that the desired oligomer concentration is present in the outflowing product stream after the alkene stream has been passed once through the reactor ("in a single pass"). This optimization step will normally be carried out from scratch in each individual case, and the reaction parameters will be optimized in many preliminary experiments. Under these circumstances, however, the degree of utilization achieved is not yet satisfactory.

It is an object of the present invention to provide a heterogeneously catalyzed adiabatic process for preparing alkene oligomers in which, at high conversion and high product selectivity, the temperature in the reactor can be controlled more flexibly than in the known processes of this type.

BRIEF DESCRIPTION OF THE DRAWINGS

FIG. 1 shows a flow diagram of an apparatus in which a process of preparing essentially unbranched oligomers of alkenes can be carried out.

We have found that this object is achieved by a process for preparing essentially unbranched oligomers of alkenes having from 4 to 6 carbon atoms starting from the alkenes or a hydrocarbon stream comprising such alkenes over a nickel-containing heterogeneous catalyst in an adiabatically operated reactor at from 20 to 300° C. and pressures of from 1 to 100 bar, in which a first substream of the output from the reactor is worked up to isolate the oligomers and the second substream is recirculated together with fresh alkene or a fresh hydrocarbon stream comprising such alkenes to the reactor.

For the purposes of the present invention, "oligomers" are dimers, trimers and higher products of the intermolecular addition reaction of alkenes having from 4 to 6 carbon atoms and have up to 18, preferably 12 and particularly preferably 8, carbon atoms.

The present invention is based on the recognition that the activity of the nickel catalysts used, the total conversion and, in particular, the selectivity of the process are, within wide limits, not adversely affected by oligomeric products formed in the process being mixed with the oligomer-free starting alkene and the mixture then being passed through the reactor.

Suitable catalysts are nickel-containing catalysts in general which are known to result in little oligomer branching: cf., for example, Catalysis Today, 6, 329 (1990), in particular pages 336–338, and also the references cited with regard to the prior art in WO-A 95/14647 and the earlier German patent application having the file number 199 57 173.2, with these references in particular being hereby expressly incorporated by reference.

Examples of such nickel-containing oligomerization catalysts, in which the nickel is generally present in oxidic form, are:

nickel on silicon dioxide, nickel on silicon dioxide-aluminum oxide, nickel on silicon dioxide-aluminum oxide sheet silicates, e.g. mica and clays, in particular montmorillonites, nickel on zeolite supports, e.g. mordenite, faujasite, zeolite X, zeolite Y, zeolite ZSM-5 or other zeolites of the ZSM type, zeolites having the MCM-41 structure or the CZS-1 structure, nickel on aluminum oxide, if desired together with anions of, especially, inorganic acids such as sulfuric, phosphoric or boric acid, nickel on zirconium oxide which has been treated with acids such as sulfuric acid, phosphoric acid or boric acid, $NiO/ZrO_2/SO_4/SiO_2$ systems, nickel on sulfated titanium dioxide.

The nickel-containing oligomerization catalysts used according to the present invention will hereinafter be referred to as "Ni catalysts" for short.

In a preferred embodiment of the process of the present invention, the oligomerization is carried out in the liquid phase using the Ni catalysts described and claimed in WO-A 95/14647 and the earlier German patent application having the file number 199 57 173.2. For this reason, the information regarding the process and the Ni catalysts in these publications is hereby expressly incorporated by reference.

The catalytically active composition of the Ni catalysts described in WO-A 95/14647 consists essentially, i.e. disregarding impurities which have been introduced by way of starting materials or process chemicals in the production of the Ni catalysts, of nickel oxide, silicon dioxide, titanium dioxide and/or zirconium dioxide plus, if desired, aluminum oxide. These Ni catalysts contain from 10 to 70% by weight of nickel oxide, from 5 to 30% by weight of titanium dioxide and/or zirconium dioxide, from 0 to 20% by weight of aluminum oxide and as balance to 100% by weight silicon dioxide. They are obtained by precipitation of the Ni catalyst composition at pH 5–9 by adding an aqueous solution comprising nickel nitrate to an alkali metal water glass solution which further comprises titanium dioxide and/or zirconium dioxide. The Ni catalyst composition obtained in this way is subsequently filtered off, dried and heat-treated at from 350 to 650° C.

The Ni catalysts of the earlier German patent application number 199 57 173.2 are essentially aluminum oxide which has been treated with a nickel compound and a sulfur compound so that the finished Ni catalyst has a molar ratio of sulfur to nickel of from 0.25:1 to 0.38:1.

Ni catalysts used according to the present invention are preferably employed in a fixed bed and are therefore preferably in the form of shaped bodies: e.g. pellets (5 mm×5 mm, 5 mm×3 mm, 3 mm×3 mm), rings (7 mm×7 mm×3 mm, 5 mm×5 mm×2 mm, 5 mm×2 mm×2 mm) or extrudates or star extrudates (1.5 mm diameter, 3 mm diameter, 5 mm diameter). The above indications of size and types of shaped body are merely by way of example and constitute no restriction of the scope of the present invention.

Specifically, in the process of the present invention the alkenes having from 4 to 6 carbon atoms (hereinafter referred to as "alkenes" for short) or mixtures of these with alkanes are reacted, preferably in the liquid phase, over the abovementioned Ni catalysts.

As alkene, preference is given to using the monounsaturated butenes, pentenes and hexenes, in particular 1-butene, 2-butene, 1-pentene, 2-pentene, 1-hexene or 3-hexene, in each case alone.

The process of the present invention permits the use of starting material streams whose alkene content is normally from 5 to 100% by weight, preferably from 30 to 100% by weight and particularly preferably from 50 to 100% by weight.

The process of the present invention is very particularly suitable for the reaction of alkenes which are present in admixture with alkanes, with both the alkenes and alkanes having, in particular, 4 carbon atoms. Suitable $C_4$-hydrocarbon streams of this type are, for example, mixtures having the following composition:

| Butane | from 10 to 90% by weight |
|---|---|
| Butene | from 10 to 90% by weight, | where the butene fraction can have the following composition:

| 1-Butene | from 1 to 50% by weight |
|---|---|
| cis-2-Butene | from 1 to 50% by weight |
| trans-2-Butene | from 1 to 99% by weight |
| Isobutene | from 1 to 5% by weight. |

A particularly preferred starting material is raffinate II. This is a butene-containing $C_4$-hydrocarbon mixture as is obtained from the $C_4$ fraction from crackers after more highly unsaturated hydrocarbons such as dialkenes, in particular 1,3-butadiene, or acetylene and subsequently the isobutene present therein have been separated off. A typical composition of a raffinate II is, for example:

| Isobutane, n-butane | 26% by weight |
|---|---|
| Isobutene | 1% by weight |
| 1-Butene | 26% by weight |
| trans-2-Butene | 31% by weight |
| cis-2-Butene | 16% by weight. |

The $C_4$-hydrocarbon streams can also, as described in DE-A 39 14 817, be freed of butadiene and sulfur-containing or oxygen-containing compounds such as alcohols, aldehydes, ketones or ethers by hydrogenation or adsorption on molecular sieves.

The oligomerization reaction generally takes place at from 30 to 280° C., preferably from 30 to 140° C. and in particular from 40 to 130° C., and a pressure of generally from 1 to 300 bar, preferably from 5 to 100 bar and in particular from 20 to 70 bar. The pressure is advantageously selected so that the starting hydrocarbon mixture is in the supercritical state or in particular in liquid state at the temperature set.

The reactor is generally a cylindrical reactor charged with the Ni catalyst; alternatively, use can be made of a cascade of a plurality of, preferably two, such reactors connected in series.

In the reactor or the individual reactors of the reactor cascade, the Ni catalyst can be located in a single fixed bed or in a plurality of fixed beds. It is also possible to use different Ni catalysts in the individual reactors of the cascade, although the use of the same Ni catalyst in all reactors of the cascade is preferred.

Furthermore, different reaction conditions in respect of pressure and/or temperature within the abovementioned pressure and temperature ranges can be set in the individual reactors of the reactor cascade.

In the reactor or the reactor cascade, the liquid reaction mixture flows, for example from the top downward, through the fixed bed of Ni catalyst.

The above-described single reactor and reactor cascade used according to the present invention for the reactions over a fixed bed of Ni catalyst will hereinafter be referred to collectively as "fixed-bed reactor".

For the purposes of the present invention, an adiabatic reaction procedure or mode of operation is, in the engineering sense, a reaction procedure or mode of operation in which, disregarding the part of the heat of reaction which is given off from the reactor to the environment by natural heat conduction and heat radiation, all of the heat of reaction is taken up by the reaction mixture and removed from the reactor together with this.

In contrast, in the isothermal reaction procedure or mode of operation, the removal of the heat of reaction from the reactor in the engineering sense is deliberately forced beyond the degree resulting from natural heat conduction or heat radiation by means of cooling or thermostating facilities. Here, a part, even if only a negligibly small part, of the heat of reaction can be virtually unavoidably transported out together with the heated reaction mixture.

As an alternative to the abovementioned fixed-bed reactors, the process of the present invention can be carried out in other reactors which are known to those skilled in the art for such heterogeneously catalyzed adiabatic reactions, for example stirred vessels or loop reactors (cf. M. Baerns, H. Hoffmann, A. Renken, Chemische Reaktionstechnik, Thieme Verlag Stuttgart 1987, page 237 ff.).

The conversion to the desired oligomers in the process of the present invention is generally from 10 to 100%, preferably from 50 to 100%, based on the alkenes used.

After leaving the single-stage or multistage reaction zone, the crude product stream is divided into a first product substream and a second product substream.

The first product substream is worked up in a manner known per se, preferably by distillation, to isolate the oligomers formed. In this work-up, residual amounts of the unreacted alkenes and, if present, the accompanying alkanes are separated off as "purge stream".

The purge stream has residual alkene contents of generally from 5 to 20% by weight and has little value as raw material for organic syntheses. It is therefore generally passed on to other uses, for instance a cracking process which can again lead to alkenes which can be utilized in the process of the present invention.

It is also possible for part or all of the purge stream to be recirculated to the first reactor. Due to its low content of reactive alkene, its effect is, for example, to increase the mass flow through the reactor, i.e. to dilute the alkene, and thus ultimately contribute to temperature control in the reactor. Furthermore, its recirculation enables the upper limit for the oligomer content in the product stream to be controlled more easily.

The second product substream is recirculated to the process with a virtually unchanged composition. The temperature of the second product substream can be brought to the desired temperature by means of apparatuses known for this purpose, e.g. heat exchangers, before being fed back into the reactor.

Since processes such as that of the present invention are usually optimized for starting materials having a particular nature and composition, it is generally necessary, inter alia for a satisfactory conversion, to increase the proportion of alkene in the second product substream back to the starting concentration, or to a value in the vicinity of this concentration, at the reactor inlet. For this purpose, according to the present invention, fresh alkene, which may be mixed with one or more alkanes, is metered into the second substream.

The ratio of the stream of fresh alkene and any recirculated part of the purge stream to the second substream which is necessary before input into the reactor can easily be determined by a person skilled in the art by means of simple preliminary tests, taking into account the desired oligomer yield and selectivity and the temperature to be set in the reactor interior for this purpose.

Furthermore, the stream of unreacted alkene having from 4 to 6 carbon atoms and recovered in the work-up of the first substrate can, together with any accompanying alkanes, be recirculated to the reactor.

The second product substream and the fresh stream of alkene can be fed into the reactor by conveying the streams simultaneously and individually, for instance via separate lines, or after prior mixing into the reactor.

Before introduction into the reactor, the temperature of each individual stream or the mixture of the streams of starting materials can be adjusted using apparatuses known per se for this purpose, e.g. heat exchangers.

If the Ni catalyst is arranged in a plurality of fixed beds in the reactor, the mixed starting material streams can be divided and introduced into the reactor at a plurality of points, e.g. upstream of a first fixed bed and/or between individual Ni catalyst beds. When using a reactor cascade, it is possible, for example, to feed all of the mixed starting material streams into the first reactor of the cascade or to divide them among the individual reactors of the cascade by means of a plurality of feed lines, as described for the case of the single reactor.

The process of the present invention gives oligomer contents in the product stream of from 5 to 100% by weight, preferably from 10 to 60% by weight and especially from 15 to 30% by weight, based on the total product stream. To achieve such an oligomer content, the weight ratio of recycle stream to fresh starting hydrocarbon stream is generally set to from 0.5 to 10, preferably from 1 to 7, in particular from 1 to 4, based on a steady-state reaction system.

There is in principle no lower limit for the oligomer content in the reaction mixture, although the process becomes uneconomical if a very low oligomer content is chosen because the recycle stream becomes excessively large. For this reason, the concentration of oligomers in the converted reaction mixture before it is divided is generally not below a lower limit of 10% by weight.

The process of the present invention makes it possible for a person skilled in the art to react flexibly to the evolution of heat in the reactor because he can choose the ratio of the feed streams to the reactor freely within wide limits. In addition, a person skilled in the art can, in particular, adapt the temperature of the second substream to his needs.

The process of the present invention also gives a person skilled in the art the opportunity of reducing the degree to which the reaction mixture is heated on passing through the reactor ("temperature rise") to a value close to pseudoisothermal reaction conditions, whereby the temperature in the reactor can be controlled even better.

The following examples illustrate the process of the present invention.

EXAMPLES

FIG. 1 shows the flow diagram of an apparatus in which the process of the present invention can be carried out. Assumption: the reaction is already in the steady state. Fresh alkene is fed via (1) and heat exchanger (2) to the reactor (3). Part of the crude product stream in line (4) is recirculated via line (4a) without work-up to the reactor. The other part of the crude product stream is conveyed via (4b) to the column (5) where it is fractionated into the oligomeric products (6) and a top product (7). All or part of the top product (7) is discharged from the process via (7b), and any remaining part is recirculated via (7a) together with the fresh alkene (1) and the substream from (4a) via the heat exchanger to the reactor.

A) Ni Catalysts

Ni Catalyst I

A material having the composition 50% by weight of NiO, 12.5% by weight of $TiO_2$, 33.5% by weight of $SiO_2$ and 4% by weight of $Al_2O_3$ as described in WO-A 95/14647 was, as described there, shaped to give 3 mm star extrudates.

Ni Catalyst II

A material having the composition 8.9% by weight of Ni, 1.6% by weight of S and the balance to 100% by weight of $Al_2O_3$ as described in the earlier German patent application number 199 57 173.2 was, as described there, produced in the form of 3 mm star extrudates.

Ni Catalyst III

A material having the composition 50% by weight of NiO, 12.5% by weight of $TiO_2$, 33.5% by weight of $SiO_2$, 4% by weight of $Al_2O_3$ as described in WO-A 95/14647 was, as described there, processed to give an unshaped spray-dried powder (particle size: 100–350 μm).

B) Hydrocarbons Having from 4 to 6 Carbon Atoms Used

The raffinate II used had the following composition:

| | |
|---|---|
| Isobutane | 3% by weight |
| n-Butane | 15% by weight |
| Isobutene | 2% by weight |
| 1-Butene | 30% by weight |
| trans-2-Butene | 32% by weight |
| cis-2-Butene | 18% by weight. |

The "$C_6$ mixture" used had the following composition:

| | |
|---|---|
| 1-Hexene | <0.1% by weight |
| trans-2-Hexene | <0.1% by weight |
| cis-2-Hexene | <0.1% by weight |
| trans-3-Hexene | 86.2% by weight |
| cis-3-Hexene | 12.2% by weight |
| 2-Methyl-2-pentene | 1.1% by weight |
| Pentenes | 0.5% by weight. |

C) Oligomerizations

Example 1

Raffinate II as feed was reacted over a 22 cm fixed bed of 83 g of Ni catalyst I in a tube reactor (internal diameter: 28 mm, length: 50 cm) in a single pass or with recirculation. Further test parameters and the results of the experiments are shown in Table 1.

TABLE 1

| | T [° C.] | Feed [g/h] | Recirculation [g/h] | Yield [% by weight] | $C_8$ Selectivity [%] |
|---|---|---|---|---|---|
| Without | 80 | 40 | 0 | 28.1 | 68.7 |
| recircula- | 80 | 66 | 0 | 24 | 72.1 |
| tion | 80 | 115 | 0 | 17.1 | 77.9 |
| With | 80 | 40 | 820 | 27.6 | 70 |
| recircula- | 80 | 62 | 870 | 23 | 73.7 |
| tion | 80 | 100 | 840 | 17.9 | 77.3 |

Explanation of terms/abbreviations used in the table:

| | |
|---|---|
| T | Reaction temperature |
| Recirculation | Recirculation of an oligomer-containing substream according to the present invention |
| Yield | Yield of oligomers based on the total crude product output |
| $C_8$ selectivity | Proportion of (here) $C_8$-isomers in the oligomers in the total product stream |

Example 2

Raffinate II as feed was reacted over a 23 cm fixed bed of 95 g of Ni catalyst II in a tube reactor (internal diameter: 28 mm, length: 50 cm) in a-single pass or with recirculation. Further test parameters and the results of the experiments are shown in Table 2.

TABLE 2

| | T [° C.] | Feed [g/h] | Recirculation [g/h] | Yield [% by weight] | $C_8$ Selectivity [%] |
|---|---|---|---|---|---|
| Without | 75 | 100 | 0 | 31.1 | 83.9 |
| recirculation | 85 | 80 | 0 | 34 | 83 |
| With | 75 | 100 | 720 | 29 | 84.5 |
| recirculation | 85 | 80 | 710 | 32.5 | 83.5 |

Explanation of the terms/abbreviations used in the table: cf. Example 1.

Example 3

20 g of raffinate II as feed were reacted for 16 hours at 80° C. in a stirred vessel using 2 g of Ni catalyst III. The yield of oligomers based on the total crude product output was 19% by weight; the proportion of $C_8$-isomers in these oligomers was 75.1%.

67 g of raffinate II as feed were reacted at 37° C. over 30 g of Ni catalyst III in a fluidized bed, with the feed flowing into the Ni/catalyst from below and thereby suspending it to a height of 29 cm. The recirculation was 960 g/h. The yield of oligomers based on the total crude product output was 23.4% by weight; the proportion of $C_8$-isomers in these oligomers was 73.9%.

Example 4

$C_6$ mixture as feed was reacted over a 75 cm fixed bed of 880 g of Ni catalyst I in a tube reactor (internal diameter: 48 mm, length: 90 cm) in a single pass or with recirculation. Further test parameters and the results of the experiments, especially the selectivity in respect of the $C_{12}$-isomers, are shown in Table 3.

TABLE 3

| | T [° C.] | Feed [g/h] | Recirculation [g/h] | Yield [% by weight] | $C_{12}$ Selectivity [%] |
|---|---|---|---|---|---|
| Without | 50 | 528 | 0 | 22.9 | 80.7 |
| recirculation | 50 | 142 | 0 | 36.8 | 75.6 |
| With | 50 | 45 | 406 | 46.1 | 73.8 |
| Recirculation | 50 | 163 | 812 | 28.4 | 77.4 |

Explanation of the terms/abbreviations used in the table: cf. Example 1.

We claim:

1. A process for preparing essentially unbranched oligomers of alkenes having from 4 to 6 carbon atoms comprising
    passing a hydrocarbon stream comprising one or more alkenes having from 4 to 6 carbon atoms over a nickel-containing heterogeneous catalyst in an adiabatically operated reactor at from 20 to 300° C. and a pressure of from 1 to 100 bar to form a crude product stream comprising one or more oligomers,
    dividing the crude product stream into a first substream and a second substream,
    isolating the oligomers from the first substream, and
    recirculating the second substream through the reactor after adding additional alkene to the second substream.

2. The process as claimed in claim 1, wherein isolating the oligomers includes at least separating unreacted alkenes from the first product stream, said process further comprising
    recirculating the unreacted alkenes into the reactor.

3. The process as claimed in claim 1, wherein the first substream is from 1 to 50% by weight of the crude product stream from the reactor.

4. The process as claimed in claim 1, wherein the first substream is from 1 to 20% by weight of the crude product stream from the reactor.

5. The process as claimed in claim 1, wherein the first substream is from 1 to 10% by weight of the crude product stream from the reactor.

6. The process as claimed in claim 1, wherein the hydrocarbon stream comprises at least one alkene selected from the group consisting of n-butene, n-pentene and n-hexene.

7. The process as claimed in claim 1, wherein the crude product stream comprises from 1 to 80% by weight of the oligomers.

8. The process as claimed in claim 1, wherein the crude product stream comprises from 10 to 50% by weight of the oligomers.

9. The process as claimed in claim 1, wherein the crude product stream comprises from 15 to 25% by weight of the oligomers.

10. The process as claimed in claim 1, wherein the the additional alkene is present in a weight ratio of from 1:1 to 50:1, relative to the second substream.

11. The process as claimed in claim 1, wherein the the additional alkene is present in a weight ratio of from 2:1 to 20:1, relative to the second substream.

12. The process as claimed in claim 1, wherein the the additional alkene is present in a weight ratio of from 5:1 to 20:1, relative to the second substream.

13. The process as claimed in claim 1, wherein the oligomers are linear.

14. The process as claimed in claim 1, wherein the hydrocarbon stream is passed over the nickel-containing heterogeneous catalyst in the liquid phase.

15. The process as claimed in claim 1, wherein the hydrocarbon stream further comprises one or more alkanes.

16. The process as claimed in claim 1, wherein the hydrocarbon stream is a $C_4$ hydrocarbon stream.

17. The process as claimed in claim 1, wherein isolating the oligomers from the first substream comprises distilling the first substream.

18. The process as claimed in claim 17, wherein distilling forms a purge stream comprising one or more unreacted alkenes.

19. The process as claimed in claim 18, wherein the purge stream comprises from 5 to 10% by weight of unreacted alkenes.

20. The process as claimed in claim 1, wherein the alkene is a $C_4$ alkene and the oligomer is a $C_8$ linear oligomer.

* * * * *